United States Patent
Chen (10) Patent No.: US 6,829,327 B1
(45) Date of Patent: Dec. 7, 2004

(54) TOTAL-REFLECTION X-RAY FLUORESCENCE APPARATUS AND METHOD USING A DOUBLY-CURVED OPTIC

(75) Inventor: Zewu Chen, Ballston Lake, NY (US)

(73) Assignee: X-Ray Optical Systems, Inc., East Greenbush, NY (US)

( * ) Notice: Subject to any disclaimer, the term of this patent is extended or adjusted under 35 U.S.C. 154(b) by 151 days.

(21) Appl. No.: 09/667,966

(22) Filed: Sep. 22, 2000

(51) Int. Cl.[7] .............................................. G01N 23/223
(52) U.S. Cl. ............................... 378/44; 378/82; 378/84
(58) Field of Search ............................. 378/44, 45, 70, 378/82, 84, 145

(56) References Cited

U.S. PATENT DOCUMENTS

| | | | |
|---|---|---|---|
| 3,777,156 A | 12/1973 | Hammond et al. | 378/84 |
| 4,331,870 A | 5/1982 | Weichert | 250/280 |
| 4,599,741 A | 7/1986 | Wittry | 378/85 |
| 4,649,557 A * | 3/1987 | Hornstra et al. | 378/84 |
| 4,882,780 A | 11/1989 | Wittry | 378/84 |
| 5,249,216 A * | 9/1993 | Ohsugi et al. | 378/46 |
| 5,742,658 A * | 4/1998 | Tiffin et al. | 378/44 |
| 5,892,809 A * | 4/1999 | Wittry | 378/85 |
| 6,236,710 B1 * | 5/2001 | Wittry | 378/84 |
| 6,285,506 B1 * | 9/2001 | Chen | 359/642 |
| 6,317,483 B1 * | 11/2001 | Chen | 378/84 |
| 6,498,830 B2 * | 12/2002 | Wittry | 378/84 |

FOREIGN PATENT DOCUMENTS

| | | | |
|---|---|---|---|
| DE | 85 34 299.8 | 6/1985 | G01N/23/223 |
| DE | 0 456 897 A1 | 6/1990 | G01N/23/223 |
| JP | 05333868 | 12/1993 | G01N/23/20 |

OTHER PUBLICATIONS

Araj, et al., pending U.K. patent application entitled "X-ray analysis apparatus", application No. 9307344.3, filed Apr. 7, 1993.
Chen et al., "Microprobe x-ray fluorescence with the use of point-focusing diffractors", Appl. Phys. Lett., vol. 71, No. 13, Sep. 29, 1997, pp. 1884–1886.

* cited by examiner

*Primary Examiner*—David V. Bruce
*Assistant Examiner*—Therese Barber
(74) *Attorney, Agent, or Firm*—Kevin P. Radigan, Esq.; Heslin Rothenberg Farley & Mesiti P.C.

(57) ABSTRACT

An improved total-reflection x-ray fluorescence (TXRF) apparatus using a doubly-curved optic is presented for use in detecting foreign matter on surfaces, for example, semiconductor wafers. The apparatus includes an x-ray source, a doubly-curved x-ray optic for diffracting and focusing the x-rays, a surface onto which at least some of the diffracted x-rays are directed, and an x-ray detector for detecting resultant x-ray fluorescence emitted by any foreign matter present on the surface One or more apertures may be provided for limiting the dispersion angle of the x-rays. The crystal or multi-layer doubly-curved optic typically adheres to Bragg's law of x-ray diffraction may be curved to a toroidal, ellipsoidal, spherical, parabolic, hyperbolic, or other doubly-curved shape. An apparatus for diffracting x-rays is also presented. The apparatus includes an x-ray source and image defining an optic circle of radius $R_1$ an x-ray optic having a surface of radius $R_P$ and a plurality of atomic planes which intersect the surface at an angle $\alpha$, wherein the radius of the atomic planes $R_P$ is defined by the equation $R_P = 2R \cos \alpha$. This diffracting apparatus may be used in a TXRF apparatus.

43 Claims, 8 Drawing Sheets fig. 2 fig. 3 fig. 4A fig. 4B

TOTAL-REFLECTION X-RAY FLUORESCENCE APPARATUS AND METHOD USING A DOUBLY-CURVED OPTIC

FIELD OF THE INVENTION

The present invention relates to a total-reflection fluorescence apparatus with a doubly-curved crystal optic to improve the detection limit for ultra-trace analysis of contaminants and impurities on a surface.

BACKGROUND OF THE INVENTION

Total-reflection x-ray fluorescence (TXRF) is a surface analytical technique for elemental analysis of particles, residues and impurities on a smooth surface. In particular, the TXRF method provides an effective means for detecting materials on surfaces that are of different composition than the composition of the surface. In this method, x-rays are directed onto a surface, typically an optically-reflective surface, with a grazing incident angle smaller than the total-reflection critical angle and are essentially totally reflected. Since the x-ray photons are totally reflected, very little x-ray photons are absorbed and scattered by the reflection medium. In contrast, foreign matter, such as particles, impurities, or contaminants, on the surface can absorb x-ray photons and produce characteristic secondary fluorescence x-rays which can be detected. Since little scattering and absorption by the reflection surface occurs, the fluorescence spectrum from the surface material itself is very low and little or no undesirable background fluorescent x-rays from the surface material is typically present. This results in very high sensitivity for measuring ultra-trace elements in, on, or near the surface of the reflection medium. This superior surface detectability makes the TXRF technique an important analytical tool for detecting foreign matter on surfaces, for example, for surface contamination control in semiconductor chip manufacture.

The rapid advance of semiconductor technology continues to demand lower detection limits for wafer surface contamination control. The detectability of TXRF apparatus based on the prior art described has approached its instrumentation limits and is unlikely to meet the demand of the semiconductor industry without significant improvement. One of the limitations of the prior art, for example, U.S. Pat. No. 5,249,216, is that only a very small fraction of the x-ray photons from the x-ray source which impinge upon the desired reflection surface contribute to the detection and measurement of the flourescent x-rays. In the prior art systems, such as the system disclosed in U.S. Pat. No. 5,246,216, most of the x-ray photons generated by the x-ray source are lost due to the poor collection capability of the optical elements, such as an aperture and monocbromator.

There are two types of monochromators used in the prior art, namely, multi-layer x-ray mirrors and crystal monochromators. Multi-layer mirrors have merit for low and medium energy x-rays due to their large d-spacing nature, that is, their large spacing between atomic planes. Multi-layer mirrors can be singly-curved in the dispersive plane and have laterally graded d-spacings thereby achieving intensity gain in the dispersive plane. However, in the direction perpendicular to the dispersive plane, multi-layer mirrors do not provide optical enhancement and the x-ray intensity suffers loss over the distance between the optic and the surface under examination. For example, for a multi-layer mirror designed for 9.7 keV x-rays (W $L_\beta$, line), the effective capture angle is a few tenths of a degree in the dispersive plane and about 1 degree in the transverse direction. For high energy x-ray photons, for example, 17 keV or 22 keV (Mo $K_\alpha$ or Ag $K_\alpha$, curved multi-layer mirrors do not yield satisfactory results and a flat multilayer or a flat crystal monochromator is used without providing enhancement of x-ray intensity.

SUMMARY OF THE INVENTION

The present invention addresses the limitations of the prior art and provides an effective means for focusing x-rays upon a surface so that a more effective means of detecting the presence of undesirable foreign matter is provided. In general, the present invention, provides a method and apparatus which greatly improves the effective collection solid angle of the x-ray photons from an x-ray source and directs the x-ray photons to the surface under examination. In one embodiment, this is achieved by using an innovative doubly-curved optical device, for example, one of the optics disclosed in copending U.S. patent applications Ser. No. 09/342,606 filed on Jun. 29, 1999 and Ser. No. 09/450,323, filed on Nov. 29, 1999 (the disclosures of which are totally included by reference herein). In contrast to the prior art, a doubly-curve optic not only functions as a monochromator, but also functions as a strong x-ray focuser or concentrator to increase the x-ray flux upon the surface under examination.

One embodiment of the present invention is a total-reflection x-ray fluorescence apparatus comprising an x-ray source, an x-ray optical element having atomic planes curved both in the dispersive plane and in the transverse direction, a surface onto which the x-rays are focused to effect total x-ray reflection, and an x-ray detector to detect fluorescence signals of foreign matter on, in or near the surface. The foreign matter typically comprises particles, impurities, surface contaminants, or irregular layers and other matter that absorb and diffusely scatter the primary photons in the path of incident x-rays. The doubly-curved optic device captures a wide angle of x-ray photons from the x-ray source and through diffraction forms a monochromatic fan beam that has a large convergent angle in the direction perpendicular to the dispersive plane. In the dispersive plane, the convergent angle of the fan beam is limited to an angle less than the critical angle of the reflection interface. This convergent angle typically ranges between about 0.01 to 0.20 degrees. This convergent fan beam impinges on the essentially flat optical surface with an incident angle less than the critical angle and undergoes essentially total reflection. The foreign matter that is in the path of the x-ray beam absorbs the x-ray photons and emits secondary fluorescence x-rays that can be detected by an x-ray detector. Note that "total-reflection" is a term of the art and implies that x-rays incident upon a surface arc essentially completely reflected without being absorbed or scattered by the surface. However, it is to be understood by those of skill in the art that, according to the present invention, some of the incident x-rays may not be totally-reflected from the surface but may be absorbed or scattered by any foreign matter present on the surface or by the surface itself.

The present invention also includes a doubly-curved optic having at least one set of atomic planes for diffracting x-rays ray photons which has a radius that is a function of the focal circle radius and the orientation of the atomic planes. Specifically, according to another embodiment of the invention, the radius, $R_P$, of at least one of the atomic planes of the optic is a function of the radius, R, of the focal circle and the angle of orientation of the atomic planes, α, relative to the surface of the optic, as expressed $$R_P = 2R \cos \alpha. \quad \text{Equation 1}$$

The angle α typically ranging from 0 to 20 degrees. This geometry of the atomic planes provides for improved intensity of the diffracted x-ray photons upon the surface under examination compared to prior art atomic plane geometries. The atomic planes of this embodiment of the present invention are preferably doubly-curved to form a toroidal, ellipsoidal, spherical, paraboloid, hyperboloid, or any other type of doubly-curve shape. The present invention typically exhibits "asymmetric Bragg diffraction",that is, an optic according to this aspect of the invention has a source location and an image location that are not symmetric about the optic.

These and other embodiments of this invention will become more apparent upon review of the following drawings and the attached claims.

DESCRIPTION OF ONE PREFERRED EMBODIMENT

Figure 1:
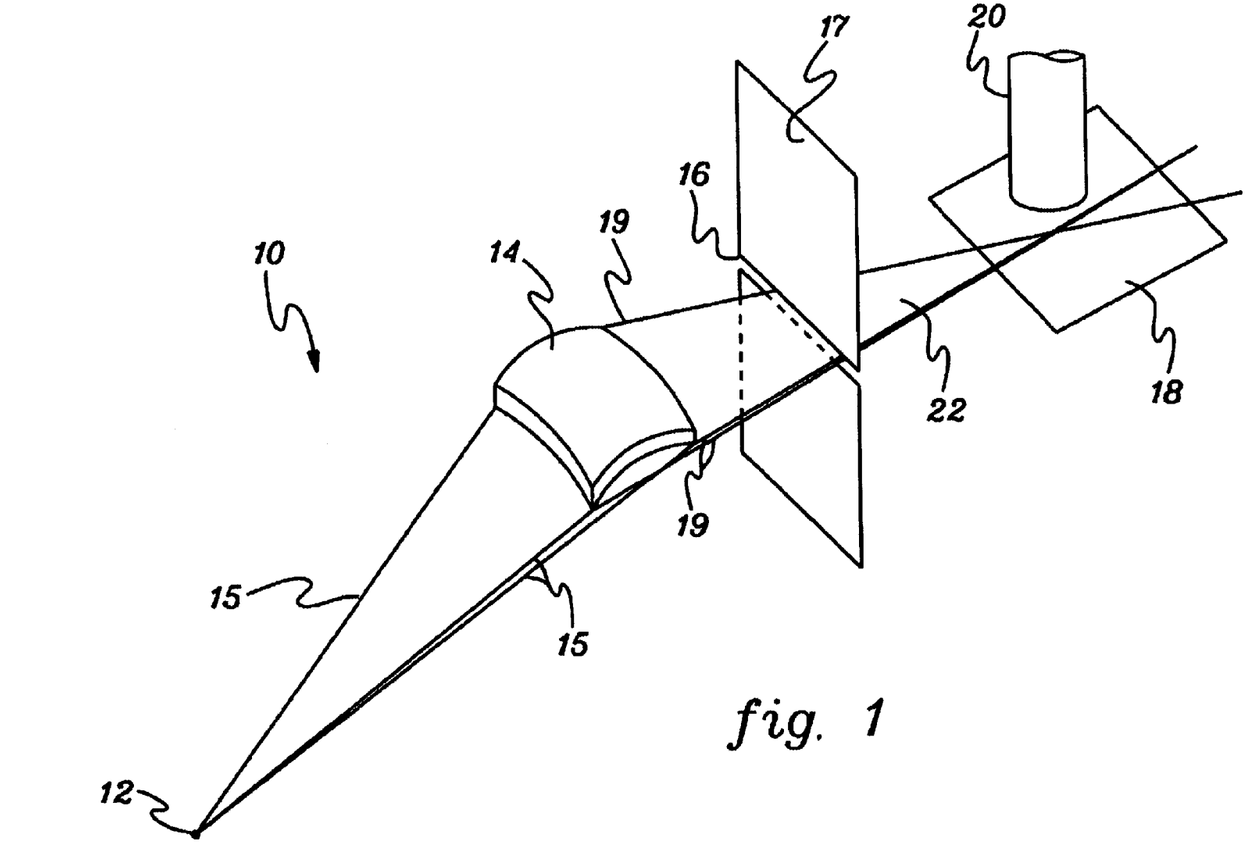
FIG. 1 is a schematic diagram showing one embodiment of a total-reflection x-ray fluorescence apparatus according to the present invention.

FIG. 1 illustrates a total-reflection x-ray fluorescence apparatus 10 in accordance with the present invention. This apparatus includes an x-ray source 12, a doubly-curved optic 14, an elongated aperture or slit 16 in an x-ray impermeable barrier 17, a surface 18 having at least some form of foreign matter (not shown), and an x-ray detector 20. X-ray photons, for example, x-ray photons having an energy between about 1 to 30 keV, emanating from the x-ray source 12 are incident upon the surface of the doubly-curved optic 14. The doubly-curved optic 14 then diffracts and focuses the x-ray photons, shown by beam 22, onto surface 18 (for example, a surface of a semiconductor wafer) to detect the presence of undesirable foreign matter on the surface 18. The surface 18 is typically movable so that the x-ray beam 22 scans the surface 18 for the presence of foreign matter. The movement of surface 18 can be regulated by an automated controller not shown.

The x-ray source 12 may be any conventional x-ray source, for example, a point source or a line source, that is appropriate for the reflective characteristics of the surface under examination. For the present invention, the x-ray wavelengths typically used depend upon the characteristic wavelength of the x-ray source used. For example, the following characteristic wavelengths may typically be used in the present invention: Cr $K_\alpha$, Cu $K_\alpha$, $WL_\beta$, Mo $K_\alpha$, or Ag $K_\alpha$ lines. One preferred source of x-rays that can be used for the present invention is a high-power rotating-anode x-ray source with a point mode, such as a Rigaku rotating-anode x-ray generator that delivers maximum power of 3 kW with effective source size of 0.2 mm×0.2 mm. Another x-ray source that can be used is a low-power compact x-ray source, for example, an Oxford XTG5011 with 50 W and 0.12 mm source size. Though the x-rays emanating from source 12 typically propagate in all directions, in FIG. 1 the boundaries of the x-rays which are incident upon the concave surfaces of optic 14 are identified by lines 15.

The x-ray optic 14 is preferably a doubly-curved optic, for example, one of the doubly-curved optics disclosed in co-pending applications 09/342,606 and 09/450,323 referenced above,or the optic may be one of the optics described below. "Doubly-curved" optics are optics having atomic planes or multi-layers which are curved in two orthogonal directions, typically referred to as the dispersion direction and the transverse direction. Doubly-curved optics are capable of diffracting or monochromatizing x-rays in a fashion similar to single-curved optics; but, unlike single-curved optics, doubly-curved optics can provide larger collection solid angles and 3-D x-ray focusing. The doubly-curved optics that can be used as optic 14 have atomic planes that may be curved to form a toroidal, ellipsoidal, spherical, parabolic, or hyperbolic shape, though any other doubly-curved shape may be used. The doubly-curved optic 14 may be a crystal optic, for example, a quartz crystal optic, or a multi-layer optic, for example, a tungsten-carbide multi-layer optic.

The x-ray optic 14 employs Bragg's law in diffracting and focusing the x-rays from the source, that is, the optic is designed to adhere to the equation $$2d \sin \theta = n\lambda \quad \text{Equation 2}$$

The variable λ is the x-ray wavelength, d is the spacing of atomic or diffraction planes of the optic, θ is the incident angle of the x-rays with respect to the diffraction planes, and n is the diffraction order. The d spacings for natural crystals and most synthetic crystals are constant. In order to diffract x-rays of the same wavelength efficiently, .a crystal optical element must have a near constant incident angle with respect to the diffraction planes of the crystal on every point of the surface. Only x-ray photons 22 with wavelength λ which satisfy the Bragg law (Equation 2) are diffracted by the crystal atomic planes of optic 14 and are refocused on to the surface 18. The boundary of these diffracted x-rays is identified by lines 19.

Figures 8, 9:
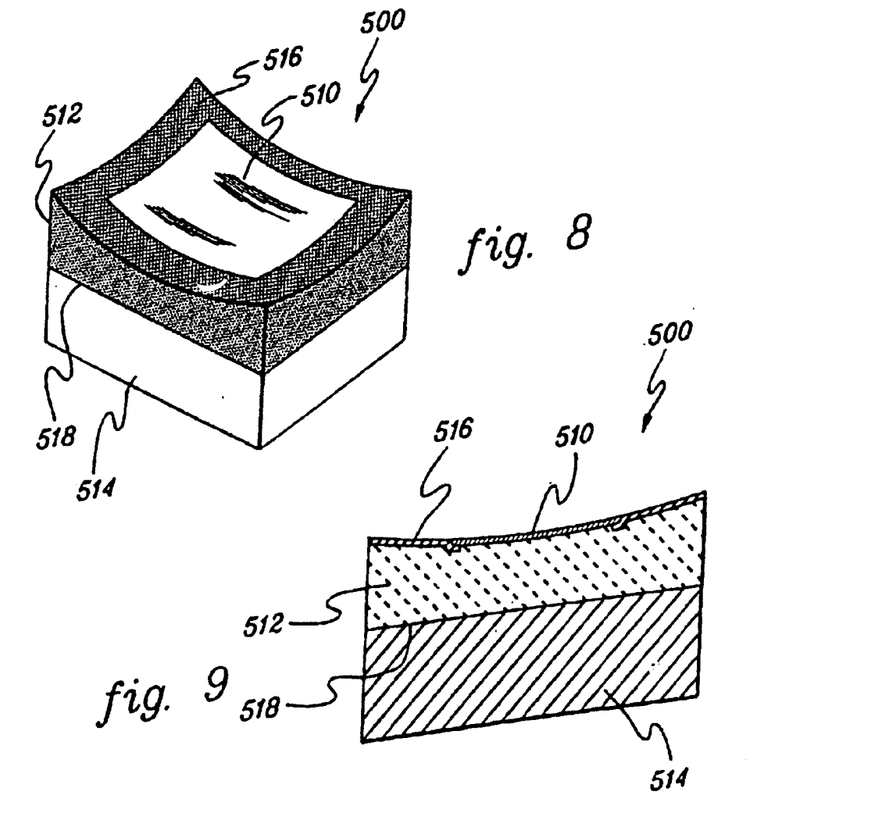
FIG. 8 shows a simple form of an x-ray optic of the present invention having a flexible layer comprising an optically smooth surface, a thick epoxy layer and a flat backing plate.
FIG. 9 shows a vertical section view of FIG. 8.
Figure 10:
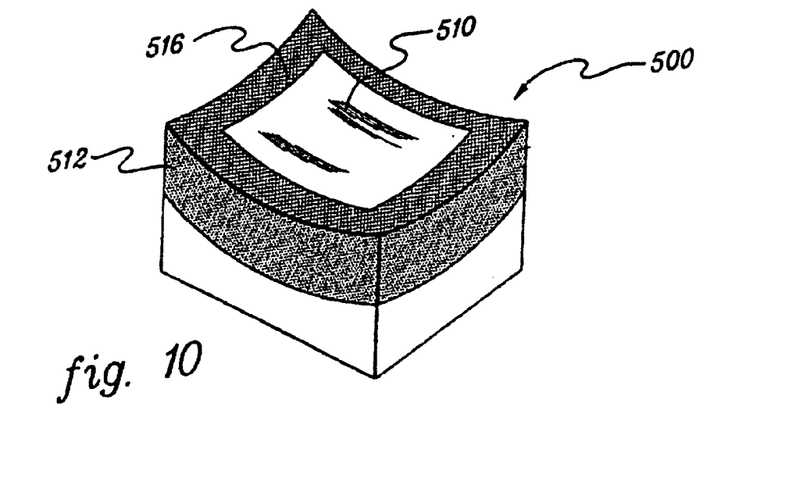
FIG. 10 shows a similar optic with a flexible layer comprising an optically smooth surface, a thick epoxy layer and a concave backing plate.

For example, as disclosed in the incorporated, commonly owned application Ser. No. 09/342,606, now U.S. Pat. No. 6,285,506, such a device 500 is shown in FIG. 8 and comprises a flexible layer 510, a thick epoxy layer 512 and a backing plate 514. The structure of the device is shown by the vertical cross-sectional view in FIG. 9. In this device, the epoxy layer 512 holds and constrains the flexible layer 510 to a selected geometry having a curvature. Preferably, the thickness of the epoxy layer is greater than 20 µm and the thickness of the flexible layer is greater than 5 µm. Further, the thickness of the epoxy layer is typically thicker than the thickness of the flexible layer. The flexible layer can be one of a large variety of materials, including: mica, Si, Ge, quartz, plastic, glass etc. The epoxy layer 512 can be a paste type with viscosity in the order of 103 to 104 poise and 30 to 60 minutes pot life. The backing plate 514 can be a solid object that bonds well with the epoxy. The surface 518 of the backing plate can be flat (FIG. 9) or curved as shown in FIG. 10, and its exact shape and surface finish are not critical to the shape and surface finish of the flexible layer. This is contrasted with standard fabrication practices which require a backing plate with a surface that is exactly the desired shape of the device. Another drawback to the standard approach is that each device requires a specially prepared backing plate. In the invention disclosed here, a specially prepared backing plate is not required.

The surrounding of the flexible layer may be a thin sheet of protection material 516, such as a thin plastic, that is used around the flexible layer edge (see FIG. 9). The protection material protects the mold so that the mold is reusable. The protection material would not be necessary for a mold that is the exact size or smaller than the flexible layer or for a sacrificial mold.

In this method, the flexible layer's final curvature is determined by the curvature of the curved surface of the mold (not shown) and not directly by the shape of the backing plate. Therefore the curvature and the surface finish of the backing plate arc not critical to the curvature and surface finish of the flexible layer. The curved surface of the mold can be convex or concave and toroidal, spherical, ellipsoid, or other optical surfaces, and hence the flexible layer can be curved to any of these geometries.

In one embodiment, the minimum thickness x of said adhesive layer is greater than or equal to 20 µm and the thickness y of the flexible layer is greater than or equal to 5 µm. The optical layer may be a crystal, and the adhesive layer an epoxy, wherein x is between 0.1 mm and 1 mm and y is between 10 µm and 50 µm.

Additional details regarding this optic can be found throughout U.S. Pat. No. 6,285,506.

In one embodiment of the invention, the total-reflection x-ray fluorescence apparatus includes an aperture 16 for limiting the convergent angle of the diffracted x-rays. This aperture is typically positioned between the x-ray optic 14 and the optical reflection surface 18 being examined, but the aperture 16 may also be positioned between the source 12 and the optic 14. The aperture may also be placed in both positions. Though this aperture may take any desired shape, the aperture is preferably an elongated slot. The slot is typically aligned essentially parallel to the surface under examination. The elongated slot is typically between about 10 and 100 mm in length and about 0.1 to 0.5 mm in width, but its dimensions are typically governed by the dimensions and geometry of the optic used. The aperture produces a convergent angle in the dispersion plane for the diffracted x-rays which is less than the critical angle of incidence for the surface to ensure the total reflection of the x-rays from the optical reflection surface for the wavelength of the x-rays.

The x-ray detector 20 is typically positioned to detect the x-ray fluorescence from the foreign matter present upon surface 18 which is illuminated by the incident x-rays from the optic (and one or more apertures). The sensor of the detector is typically positioned above the reflective surface, but can be positioned in any desired location relative to the surface, for example, depending upon the direction of incidence of the focused x-rays.

Figure 2:
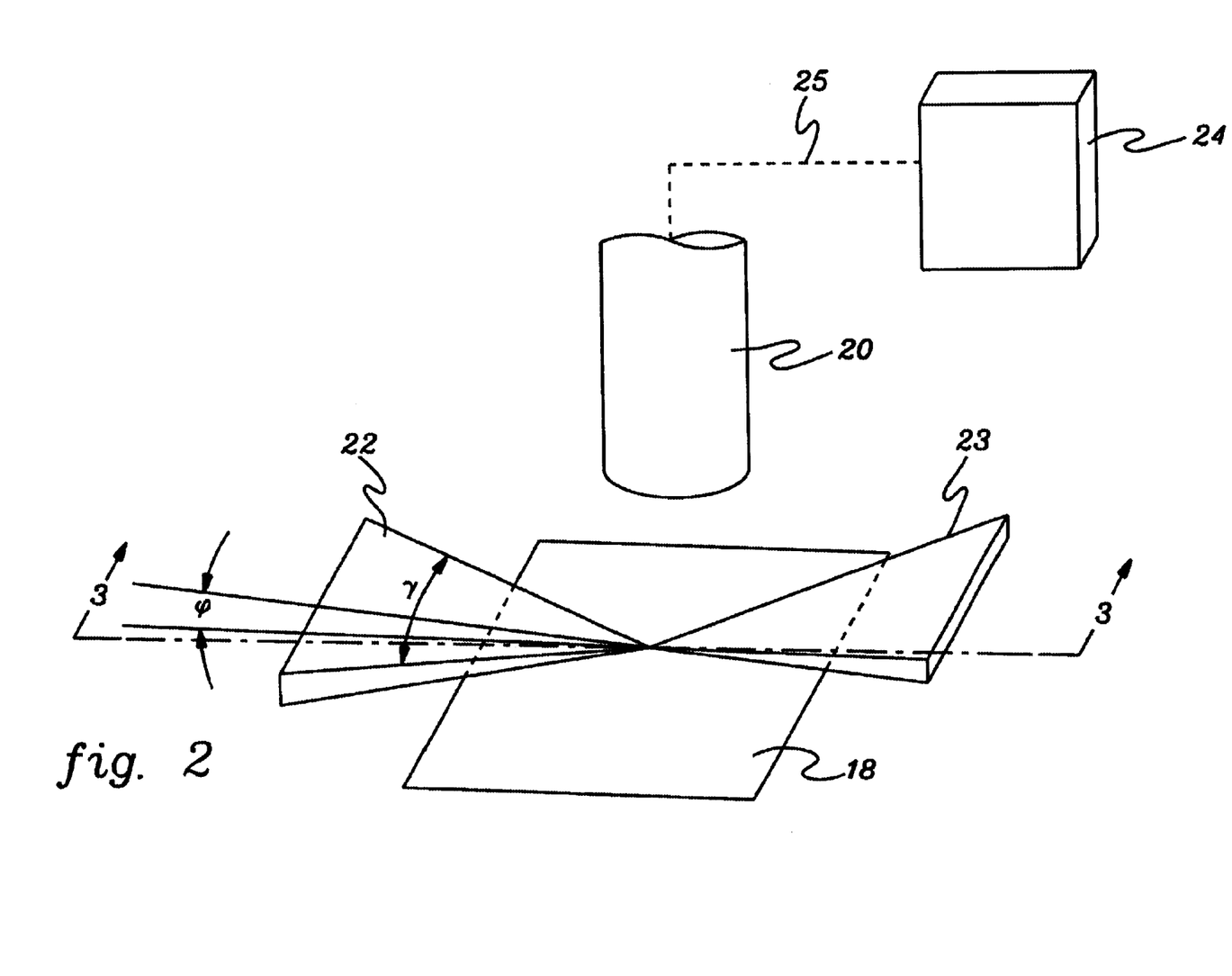
FIG. 2 shows a fan beam produced by the apparatus of FIG. 1.

FIG. 2 illustrates a detailed view of the beam 22, shown in FIG. 1, as it is reflected from optical surface 18. As shown in FIG. 2, the slit 16 in barrier 17 of FIG. 1 limits the convergent angle of the diffracted beam 22 to an angle $\phi$. The diffracted and focused beam 22 strikes the surface 18 at a grazing incident angle, $\delta$, that is less than the critical angle or total reflection, $\delta_c$, of the reflection medium for the x-ray wavelength $\lambda$. Having an incident or grazing angle $\delta$ less than $\delta_c$ ensures that incident x-rays 22 are essentially totally reflected as shown in FIG. 2 by x-ray beam 23. As a consequence, the convergent angle, $\phi$, is also typically less than the critical angle, $\delta_c$, and typically ranges from about 0.01 to 0.20°. The critical angle, $\delta_c$, typically ranges from 0.05 to 0.50°. The convergent angle in the transverse direction for the diffracted beam 22, $\gamma$, is mainly determined by the effective sizes of the optic 14 and could be up to 20° or larger, but typically ranges from 5 to 20 degrees. The x-ray detector 20 shown in FIG. 2, may be any appropriate x-ray detector, but is preferably a solid state energy dispersive detector.

Surface 18 may be any type of optically-smooth surface from which the incident x-ray photons will reflect. Typical surfaces for which the present intention can be used are semiconductor surfaces, for example, a silicon wafer, and polished quartz surfaces.

The total-refection x-ray fluorescence apparatus according to the invention also typically includes an analyzer for analyzing the x-rays. This analyzer preferably receives an electric signal form the x-ray detector which corresponds to the energy of the fluorescent x-rays emitted from the foreign matter. This analyzer typically includes some form of data manipulation capability, for example, filtering or amplification, in order to analyze and characterize the nature of the fluorescent x-rays detected by the detector. The analyzer also typically includes some form of data storage, output, and operator input. FIG. 2 also illustrates a typical data acquisition or data analyzing device or system 24 for analyzing the data signals received from x-ray detector 20. The data from detector 20 is passed to analyzer 24 via electrical connection 25.

As shown in FIG. 2, the present invention provides a localized concentration of x-ray energy to the surface under examination. Prior art total-reflection x-ray fluorescence apparatuses typically cannot provide such localized concentrated x-rays. Prior art devices typically provide an x-ray "foot print" on the surface under examination of about 10 mm×0.2 mm to 0.4 mm. The present invention can provide an x-ray foot print of about 200 microns microns×50 microns, or even about 100 microns×50 microns, or less. That is, the present invention typically provides for at least 2 orders of magnitude in improvement in focusing and concentrating x-ray photons than the prior art. In addition, the present invention can provide for the variation of the foot print size as desired, for example, from as large as 10 mm down to 100 microns and even smaller.

Figure 3:
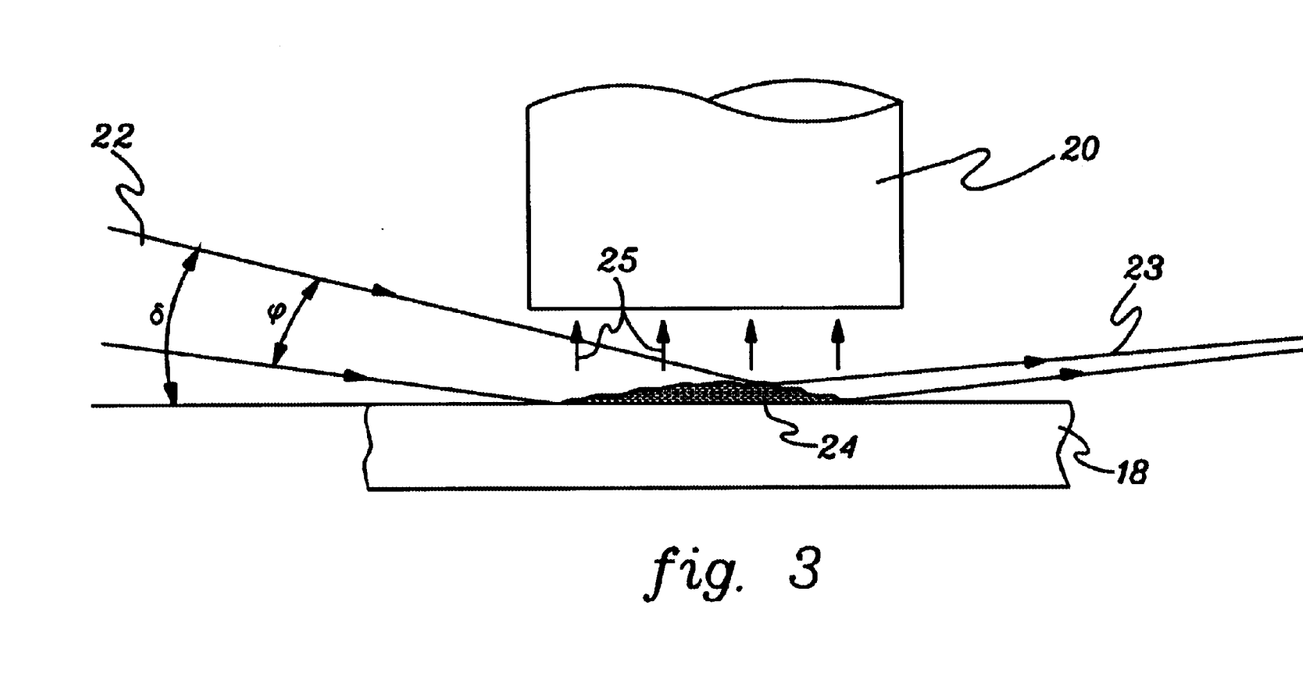
FIG. 3 shows a cross-sectional view of FIG. 2 taken along line 3—3.

FIG. 3 represents a detailed cross-sectional view of the point of impingement and ($d^\theta$ reflection of the incident beam 22 on surface 18 shown in FIG. 2 as viewed through section 3—3. The beam convergence angle $\phi$ and the maximum incident angle $\delta$ of the rays are clearly shown in FIG. 3. The foreign matter 24, which is typically too small in size to be shown in the scale of FIG. 2, is shown in the detail of FIG.

3. The foreign matter 24, such as particles or impurities, located in, on, or near the surface 18 can be excited by the x-ray photons in the path of beam 22. It is to be understood that foreign matter that is "present" on the surface 18 includes matter which is in, on, or near surface 18. The excited atoms in the foreign matter emit secondary fluorescence x-rays, indicated by arrows 25, which can be detected by the detector 20, such as a solid state x-ray detector. The fluorescence signals detected by the detector are analyzed, for example, by analyzer 25 (see FIG. 2) and the elemental concentration of the foreign matter can be determined.

Figure 4A:
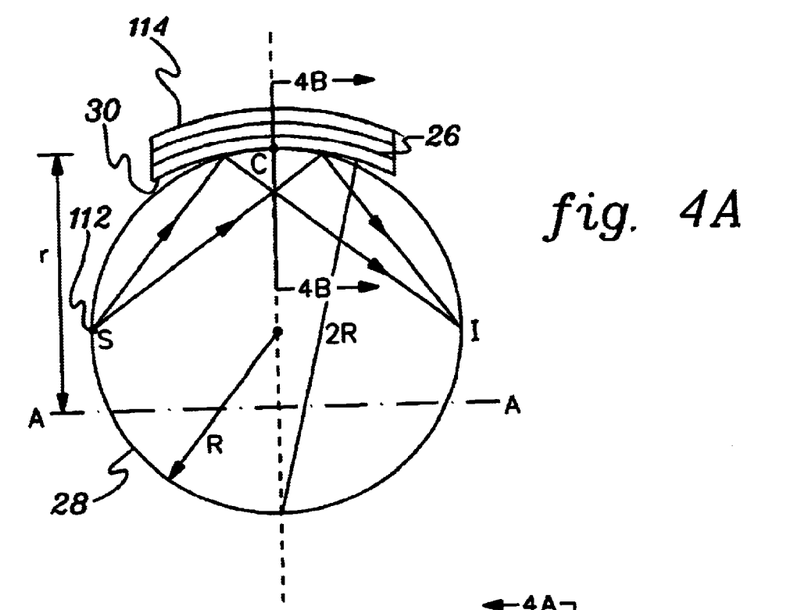
FIGS. 4A and 4B show the geometry of a toroidally curved optic with a point source according to one embodiment of the present invention.
Figure 4B:
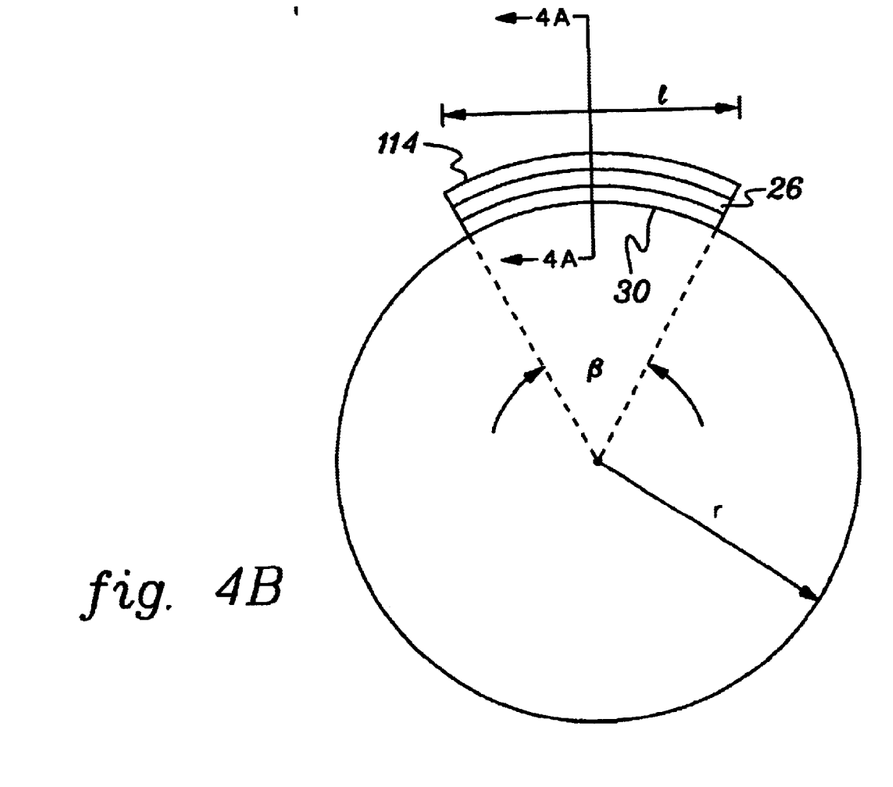

There are several possible embodiments according to the present invention. One embodiment includes a point-type x-ray source 112 and a toroidally curved crystal 114 in a configuration shown in FIGS. 4A and 4B. FIG. 4A is a cross sectional view of one type of optic 114 that can be used for the optic 14 shown in the system 10 of FIG. 1. FIG. 4B depicts a cross-sectional view of optic 114 viewed through section 4B—4B of FIG. 4A. FIG. 4A depicts a cross section of optic 114 viewed through section B—B' of FIG. 4B. Again, the optic 114 may be a crystal optic or a multi-layer optic. Note that the optic and geometry of FIGS. 4A and 4B (as well as those shown in FIGS. 5A through 7) are magnified for ease of illustration. Optic 114 typically has a thickness of only about 0.001 to 0.005 mm.

The toroidal optic 114 can be single crystal plate of silicon (Si), germanium (Ge), or a silicon-germanium crystal of the general formula $Si_{1-x}Ge_x$, where x is number less than 1. Optic 114 may also be a quartz or other crystal material. The atomic planes 26 of the crystal are typically selected to be parallel or nearly parallel to the crystal surface 30. Again, note that the spacing of the atomic planes 26 are exaggerated in FIGS. 4A and 4B. The spacing of the atomic planes (known in the art as "d-spacing") in x-ray optics such as optic 114 are measured in angstroms; typically, the d-spacing of atomic planes of optics such as optic 114 range from 1 to 20 Å.

In FIGS. 4A and 4B, the atomic planes 26 are curved to a toroidal shape that is created by rotating an arc of a radius of 2R about an axis AA' through an angle of rotation β. The position S of source 112, center of the toroidal crystal surface C, and the focus of the diffracted beam I are on the focal circle 28 with a radius of R. The optimized value of the bending radius r (shown in FIG. 4B) in the plane perpendicular to the plane of the focal circle 28 is equal or near to the value of $L_{SC} \sin(\theta_B)$, where $L_{SC}$ is the distance between the source S and the center of the toroidal surface C, and $\theta_B$ is the Bragg angle of the atomic planes for the pre-selected wavelength λ. In one embodiment, when $r=L_{SC} \sin(\theta_B)$, the rotation axis AA' becomes the line SI and the toroidal crystal provides point-to-point focusing.

For example, a point-to-point focusing Si (220) toroidal crystal optic has a bending radius 2R=512 mm in the focal circle plane and r=85 mm in the transverse direction for W $K_{\beta 1}$ x-ray photons with a pre-selected source-crystal distance $L_{SC}$=200 mm. This Si toroidal crystal provides a fan beam with a convergent angle of 20° for a crystal plate with length l=70 mm (see FIG. 4B).

The x-ray source for any of the embodiments shown in FIGS. 1 through 6 can be a high-power rotating-anode x-ray source with a point mode, such as a Rigaku rotating anode x-ray generator that delivers maximum power of 3 kW with effective source size of 0.2 mm×0.2 mm. A low-power, compact x-ray source is desirable for a compact system, for example, an Oxford XTG5011 x-ray source with 50 W and 0.12 mm source size.

Figure 5A:
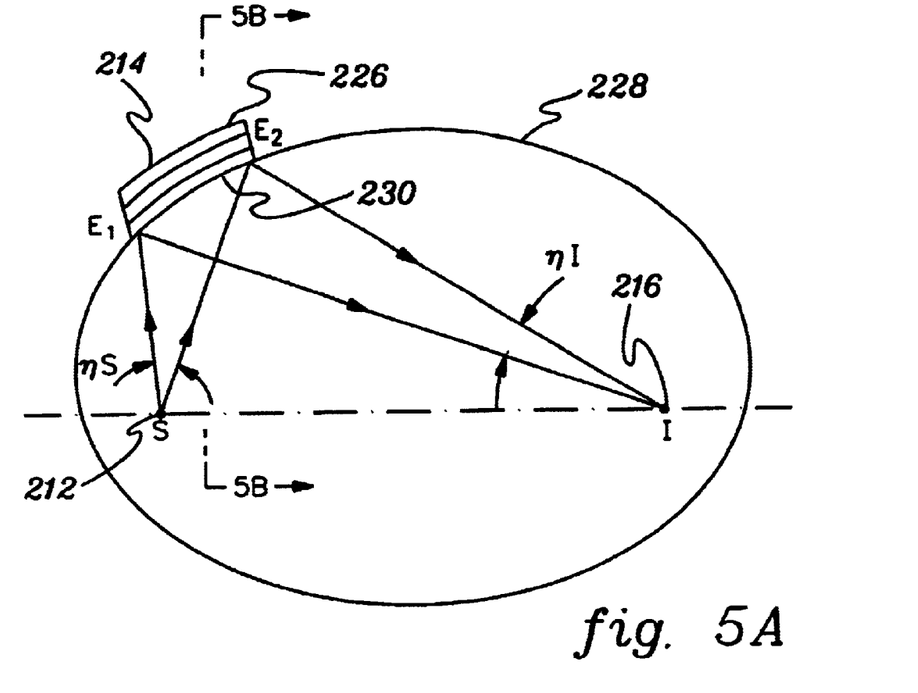
FIGS. 5A and 5B show the geometry of an ellipsoidally curved optic with a point source according to another embodiment of the present invention.
Figure 5B:
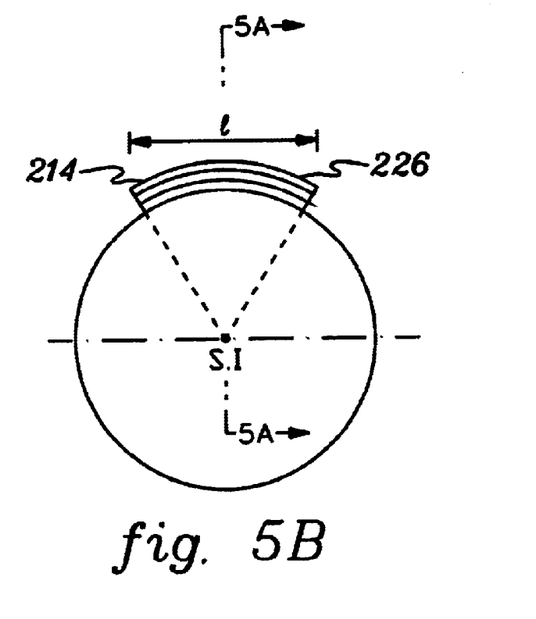

Another embodiment of the present invention includes a point-type x-ray source 212 and an ellipsoidal gradient optic 214 as depicted in FIGS. 5A and 5B. FIG. 5A is a cross sectional view of another type of optic 214 that can be used for the optic 14 shown in the system 10 of FIG. 1. FIG. 5B depicts a cross section of optic 214 viewed through section 5B—5B of FIG. 5A. FIG. 5A depicts a cross section of optic 214 a viewed through section 5A—5A of FIG. 5B. Again, optic 214 may be a crystal or multilayer optic as described with respect to FIGS. 4A and 4B. In the configuration of FIG. 5A, the x-ray source 212 is located at one focus S of the ellipsoid 228 and the image 216 is located at the other focus I. The optic 214 is defined by a segment of the ellipsoid surface 228 wherein the magnification of the optic 214 is greater than 1. The "magnification" of an optic means the ratio of the subtended angle $\eta_S$ to the subtended angle $\eta_I$ of the segment with respect to the two foci (S and I) of the ellipsoid 228. Due to the geometry of the surface 230 of optic 214, the incident angles of the x-ray photons from the source 212 vary over the length of the surface 230. The larger the magnification, the more rapid the incident angle changes per unit distance along the surface 230. In order to diffract over a relatively large angle $\eta_S$ for monochromatic x-rays and obtain a meaningful magnification, a crystal material with graded lattice spacing is used ( see the optics disclosed in co-pending application Ser. No. 09/450,323). The atomic planes 226 are typically curved to the shape of the surface 230 and the d-spacing of the planes increases from one end E1 to the opposite end E2 to account for the change of the incident angle along the surface 230 to rid maintain the desired Bragg condition(see Equation 1). The atomic planes of optic 214 are circular in the transverse direction (see FIG. 5B) and the d-spacing in this direction is relatively constant.

The variation of d-spacing illustrated in FIG. 5A can be produced by growing a crystal made of two or more elements, such as a $Si_{1-x}Ge_x$ crystal. For example, with $\eta_S=0.4°$, $\eta_I=0.1°$ and a average incident angle of 45° on the surface 30, an increase of 0.5% of d-spacing, is needed from the E1 end to the E2 end of optic 214. For a $Si_{1-x}Ge_x$ gradient crystal, the 0.5% change on the d-spacing roughly corresponds to 15% change of Ge concentration.

Figures 6A, 6B, 6C:
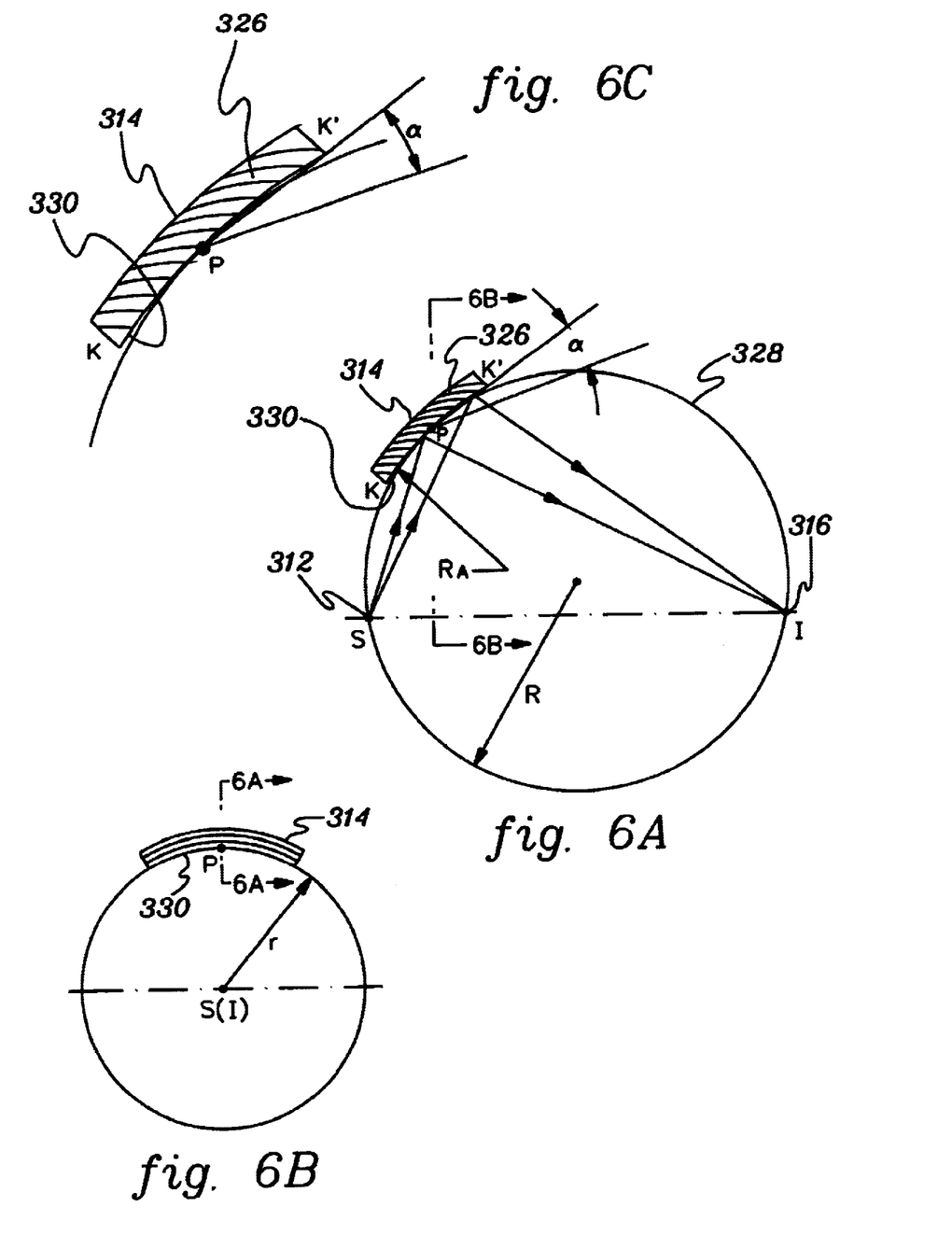
FIGS. 6A, 6B and 6C show the geometry of a doubly-curved optic based on asymmetric Bragg diffraction according to still another embodiment of the present invention.

Still another embodiment of the present invention is illustrated in FIGS. 6A, 6B, and 6C. FIG. 6A is a cross sectional view of another type of optic 314 that can be used for the optic 14 shown in the system 10 of FIG. 1. FIG. 6B depicts a cross section of optic 314 viewed through section 6B—6B of FIG. 6A. FIG. 6A depicts a cross section of optic 314 viewed through section 6A—6A of FIG. 6B. FIG. 6C is a detailed view of the surface of optic 314 about a point P. Optic 314 is typically a crystal optic as described earlier.

FIGS. 6A, 6B, and 6C illustrate x-ray optic 314 in accordance with another invention. This optic 314 may also be used in the total-reflection x-ray fluorescence apparatuses illustrated in FIG. 1. Similar to the embodiments illustrated in FIGS. 4A and 5A, the optic 314 in FIG. 6A is included within an apparatus which includes an x-ray source 312 at location S and an x-ray image 316 located at I. The optic 314, source 312, and image 316 define an optic or focal circle 328 having a radius R. The surface 330 of the optic 314 has a radius $R_p$. In the transverse plane shown in FIG. 6B, the shape of the optic 314 is defined by a circle 332 of radius r. The optic 316 has atomic planes 326 which are not parallel to the surface 330, but generally intersect the surface 330, for example, at a point P.

Unlike the optics shown earlier, in the embodiment shown in FIG. 6A, according to another embodiment of the invention, the doubly-curved optic 314 has "asymrnmctrical Bragg diffraction". Asymmetric Bragg diffraction is a term of the art which means that the incident angle and the reflection angle of the rays with respect to the optic surface are different. Asymmetric Bragg diffraction provides improved diffraction properties, for example, increased tolerance for Bragg diffraction compared to symmetric diffraction.

As shown in FIG. 6C, the diffraction planes 326 of optic 314 have an angle of inclination ax with respect to the optic's surface 330, for example, at point P, where the atomic planes intersect the surface 330. The invention illustrated in FIGS. 6A, 6B,and 6C comprises a doubly-curved optic 314 having at least one set of atomic planes for diffracting x-rays ray photons which has a radius $R_P$ that is a function of the radius of the focal circle R and the angle of orientation α of the atomic planes. Specifically, according to another embodiment of the invention, the radius, $R_P$, is given by the equation $$R_P = 2R \cos \alpha.$$  Equation 1

The angle α maybe greater than 0° and less than 90°, but is typically greater than 0° and less than 40°. This geometry of the atomic planes provides for improved diffraction and focusing of the x-ray photons upon the surface under examination, for example, increased tolerance for obtaining and maintaining Bragg diffraction, compared to prior art atomic plane geometries. The atomic planes of this embodiment of the invention are preferably doubly-curved to form a toroidal, ellipsoidal, spherical, paraboloid, hyperboloid, or any other type of doubly-curve shape. Also, in order to meet the Bragg condition, the norm, n, of the atomic diffraction plane at a surface point P is preferably located in the plane defined by points S,I, and P.

The shape of surface 330 of the optic is created by rotating the arc KK' about an axis through the source location S and the image location I having a radius r (see FIG. 6B.) As shown in FIG. 6B, in the direction perpendicular to the focal circle plane, the atomic planes are circular and relatively parallel to the surface 330.

Figure 7:
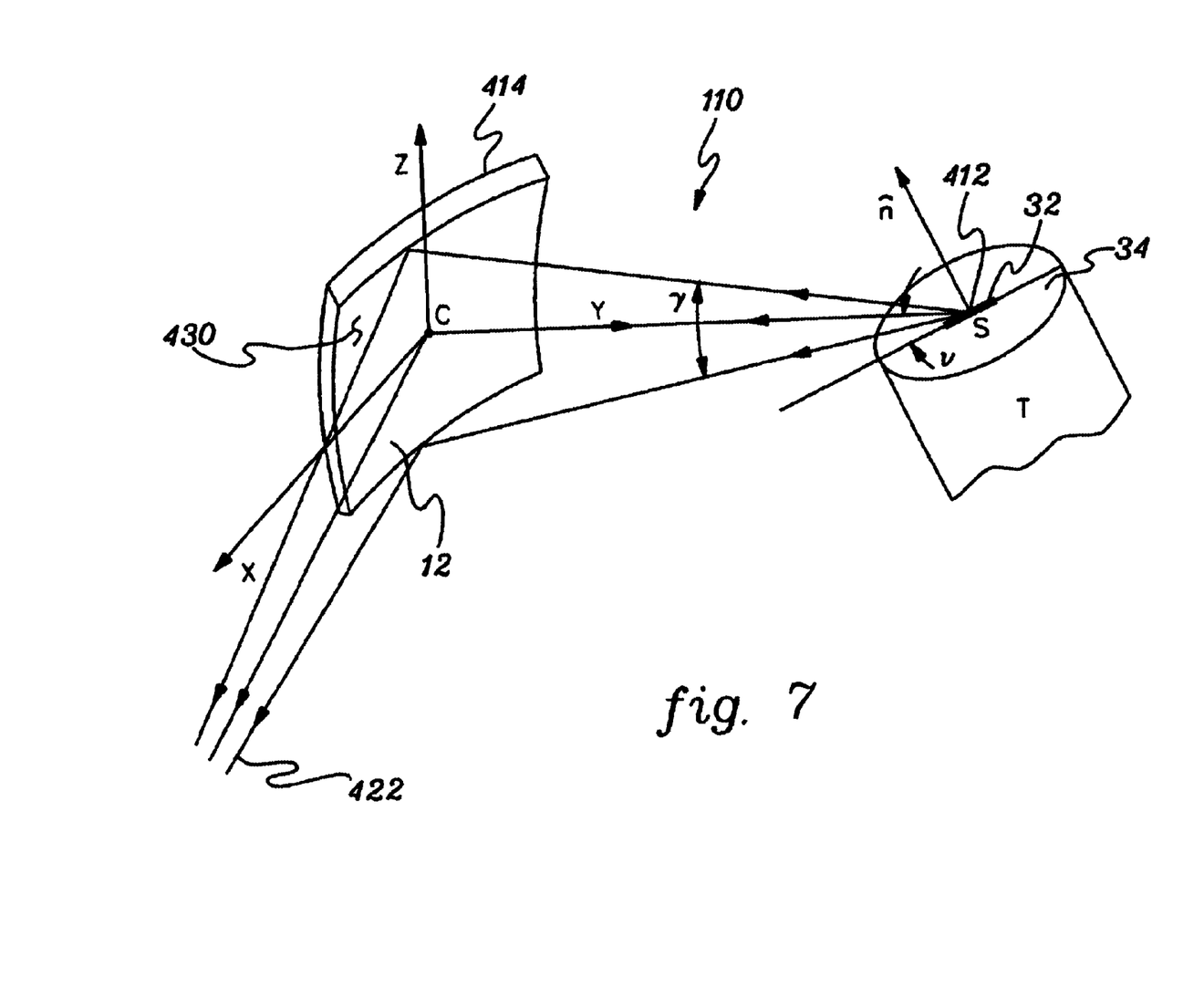
FIG. 7 shows use of a line x-ray source and a doubly-curved optic according to a further embodiment of the present invention.

A further embodiment of the present intention includes a line x-ray source as shown in FIG. 7. FIG. 7 illustrates a system 110, having a doubly-curved optic 414 and a line x-ray source 32. The surface onto which the x-rays are directed is not shown, but the diffracted and focused x-rays are generally shown by rays 422. The x-ray source 32, associated with electron beam target T, has a surface 34 having a normal $n_δ$. The optic 414 may be any type of doubly-curved optic, for example, those disclosed above and in co-pending applications Ser. Nos. 09/342,606 and 09/450,323. In the configuration shown in FIG. 7, the focal circle of the doubly-curved optic is in the XY plane and passes the center C of the crystal surface 430. For the line source 32, not all the points on the line source can typically be at the aligned position with the axis of the optic 414. For the doubly-curved optic shown, the sensitivity to misalignment in the three XYZ directions is typically quite different. In most cases, the misalignment of the source with the Y direction is relatively insensitive and the misalignment in the Z direction is also not very sensitive. However, the misalignment in the X direction is the most sensitive, because it is the dispersive direction of the diffraction plane. Therefore, the optimum orientation of the line source 32 is in the YZ plane. For line sources, such as source 32, the source is typically inclined relative to the Y axis of the optic 414. In FIG. 7, this inclination is identified by angle υ, known in the art as the "take-off angle" of the line source 32. This take-off angle u must be greater than 0° to ensure atleast some x-ray photons are directed toward the optic 414.

The line source 32 in FIG. 7 can be a sealed x-ray tubes or a rotating anode source. For example, a Philips fine-focus sealed x-ray tube can deliver 2 kW power with source size of 10 mm long and 0.05 mm wide. A Rigaku rotating anode generator can provide 18 kW power with source size of 10 mm×0.5 mm.

As described above, present invention provides methods and apparatuses for detecting foreign matter, for example, impurities or contaminants, on surfaces, in particular, semiconductor wafer surfaces, by focusing x-rays upon the surfaces and detecting the secondary x-ray reflectance emitted by the foreign matter. It is to be understood that modifications and alterations can be made to the specific apparatuses and methods disclosed in this application without deviating from the essence of the invention.

What is claimed is:

1. A total-reflection x-ray fluorescence apparatus comprising:
   an x-ray source for providing x-rays;
   a doubly-curved x-ray optic for diffracting and focusing the x-rays provided by the x-ray source;
   a surface onto which at least some of the diffracted and focused x-rays are directed; and
   an x-ray detector for detecting resultant x-ray fluorescence emitted by any foreign matter present on the surface.

2. An apparatus as recited in claim 1 wherein the doubly-curved x-ray optic is a crystal or multi-layer x-ray optic.

3. An apparatus as recited in claim 1 wherein the doubly-curved x-ray optic has one or more atomic planes.

4. An apparatus as recited in claim 3 wherein the atomic planes are curved to form a toroidal, ellipsoidal, spherical, parabolic, or hyperbolic shape.

5. An apparatus as recited in claim 1, further comprising one or more apertures for limiting a convergent angle onto the surface of the diffracted x-rays, wherein the convergent angle comprises the angle subtending the upper and lower extents of the diffracted x-rays.

6. An apparatus as recited in claim 5, wherein the one or more apertures comprise an elongated slot.

7. An apparatus as recited in claim 5, wherein the one or more apertures produce a convergent angle for the diffracted x-rays which is less than the critical angle for the total reflection of the x-rays from the surface for the wavelength of the x-rays.

8. An apparatus as recited in claim 5, wherein the one or more apertures are positioned after the x-ray optic.

9. An apparatus as recited in claim 1, wherein the doubly-curved x-ray optic employs Bragg's law in diffracting the x-rays.

10. An apparatus as recited in claim 1, further comprising an analyzer for analyzing the x-ray fluorescence detected by the detector.

11. An apparatus as recited in claim 1, wherein the surface is an optical reflection surface.

12. An apparatus as recited in claim 1, wherein the surface is a surface of a semi-conductor wafer.

13. A total-reflection x-ray fluorescence apparatus comprising:
   an x-ray source for providing x-rays;
   a doubly-curved x-ray optic for diffracting and focusing the x-rays provided by the x-ray source;
   a surface onto which at least some of the diffracted and focused x-rays are directed;
   an x-ray detector for detecting resulting x-ray fluorescence emitted by any foreign matter present on the surface; and wherein the locations of the doubly-curved x-ray optic, x-ray source, and point of impingement upon the surface define an optical circle of radius R wherein the doubly-curved x-ray optic has an optic surface of radius 2R and one or more atomic planes essentially parallel with the optic surface.

14. An apparatus as in claim 13, wherein the doubly-curved x-ray optic provides one of symmetric or asymmetric Bragg diffraction.

15. An apparatus as recited in claim 13, wherein the atomic planes are curved to form a toroidal, ellipsoidal, spherical, parabolic, or hyperbolic shape.

16. An apparatus as in claim 13, wherein the doubly-curved x-ray optic has a transverse plane perpendicular to the optic circle wherein in the transverse plane the atomic planes are circular.

17. The apparatus as recited in claim 13, wherein the doubly-curved x-ray optic comprises:
  a backing plate having a supporting surface;
  an adhesive layer disposed above said supporting surface of said backing plate, said adhesive layer having a minimum thickness x; and
  an optical layer disposed above said adhesive layer, said optical layer comprising an optical surface, said optical surface of said optical layer having a desired curvature, and said optical layer having a thickness y, wherein x>y.

18. A method for detecting presence of foreign matter on a surface by total x-ray diffraction using a doubly-curved x-ray optic, comprising:
  providing a source of x-rays;
  diffracting and focusing at least some of the x-rays using a doubly-curved x-ray optic and impinging the diffracted and focused x-rays upon the surface; and
  detecting fluorescent x-rays responsive to the impingement from any foreign matter present on the surface.

19. A method as recited in claim 18, further comprising exciting foreign matter present on the surface with the diffracted x-rays so that the foreign matter emits the fluorescent x-rays.

20. A method as recited in claim 18, further comprising passing the diffracted x-rays through at least one aperture to limit the convergent angle onto the surface of the diffracted x-rays, wherein the convergent angle comprises the angle subtending the upper and lower extents of the diffracted x-rays.

21. A method as recited in claim 20, wherein the passing through at least one aperture is practiced after the x-ray optic.

22. A method as recited in claim 18, further comprising analyzing the detected x-rays to determine the nature of the foreign matter.

23. A total-reflection x-ray fluorescence apparatus comprising:
  an x-ray source for providing x-rays;
  a doubly-curved x-ray optic for diffracting and focusing the x-rays provided by the x-ray source;
  a surface onto which at least some of the diffracted and focused x-rays are directed;
  an x-ray detector for detecting resulting x-ray fluorescence emitted by any foreign matter present on the surface; and;
  wherein the x-ray source and the point of impingement upon the surface define an optic circle of radius R, and wherein the doubly-curved x-ray optic comprises a surface and a plurality of atomic planes of radius $R_P$ which intersect the surface at an angle $\alpha$; and
  wherein the radius of the atomic planes $R_P$ of the doubly-curved x-ray optic is defined by the equation $R_P = 2R \cos \alpha$.

24. An apparatus as recited in claim 23, wherein the angle $\alpha$ is greater than 0° and less than 90°.

25. An apparatus as recited in claim 24, wherein the angle $\alpha$ is greater than 0° and less than 20°.

26. An apparatus as recited in claim 23, wherein the doubly-curved x-ray optic is curved to a toroidal, ellipsoidal, spherical, parabolic, or hyperbolic shape.

27. An apparatus as recited in claim 23, wherein the doubly-curved x-ray optic exhibits asymmetric Bragg diffraction.

28. An apparatus as recited in claim 23, wherein the doubly-curved x-ray optic also focuses the x-rays on to the surface.

29. An apparatus as in claim 28, wherein the doubly-curved x-ray optic focuses x-rays to a footprint on the surface and wherein the footprint comprises a largest dimension less than 1 mm.

30. An apparatus as in claim 29, wherein the doubly-curved x-ray optic focuses x-rays to a footprint on the surface wherein the footprint comprises a largest dimension less than 500 microns.

31. The apparatus as recited in claim 23, wherein the doubly-curved x-ray optic comprises:
  a backing plate having a supporting surface;
  an adhesive layer disposed above said supporting surface of said backing plate, said adhesive layer having a minimum thickness x; and
  an optical layer disposed above said adhesive layer, said optical layer comprising an optical surface, said optical surface of said optical layer having a desired curvature, and said optical layer having a thickness y, wherein x>y.

32. A total-reflection x-ray fluorescence apparatus comprising:
  an x-ray source for providing x-rays;
  a doubly-curved x-ray optic for diffracting and focusing the x-rays provided by the x-ray source;
  a surface onto which at least some of the diffracted and focused x-rays are directed; and
  an x-ray detector for detecting resultant x-ray fluorescence emitted by any foreign matter present on the surface;
  wherein the doubly-curved x-ray optic comprises:
    a backing plate having a supporting surface;
    an adhesive layer disposed above said supporting surface of said backing plate, said adhesive layer having a minimum thickness x; and
    an optical layer disposed above said adhesive layer, said optical layer comprising an optical surface, said optical surface of said optical layer having a desired curvature, and said optical layer having a thickness y, wherein x>y.

33. The apparatus as recited in claim 32, wherein said supporting surface of said backing plate has a curvature, said curvature of said supporting surface being different than said curvature of said optical surface of said optical layer.

34. The apparatus as recited in claim 32, wherein said adhesive comprises an epoxy material, and wherein said optically curved element further comprises a protective layer surrounding an edge of said optical layer such that said adhesive is disposed between said optical layer, with said protective layer surrounding said edge thereof, and said supporting surface of said backing plate.

35. The apparatus as recited in claim 32, wherein said minimum thickness x of said adhesive layer is greater than or equal to 20 µm; and said thickness y of said flexible layer is greater than or equal to 5 µm.

36. The apparatus as recited in claim 32, wherein said optical layer comprises a crystal.

37. The apparatus as recited in claim 36, wherein said adhesive layer is an epoxy, and wherein: x is between 0.1 mm and 1 mm and y is between 10 µm and 50 µm.

38. A method for detecting presence of foreign matter on a surface by total x-ray diffraction using a doubly-curved x-ray optic, comprising:
   providing a source of x-rays;
   diffracting and focusing at least some of the x-rays using a doubly-curved x-ray optic and impinging the diffracted and focused x-rays upon the surface, and
   detecting fluorescent x-rays responsive to the impingement from any foreign matter present on the surface;
   wherein the doubly-curved x-ray optic comprises:
      a backing plate having a supporting surface;
      an adhesive layer disposed above said supporting surface of said backing plate, said adhesive layer having a minimum thickness x; and
      an optical layer disposed above said adhesive layer, said optical layer comprising an optical surface, said optical surface of said optical layer having a desired curvature, and said optical layer having a thickness y, wherein x>y.

39. The method as recited in claim 38, wherein said supporting surface of said backing plate has a curvature, said curvature of said supporting surface being different than said curvature of said optical surface of said optical layer.

40. The method as recited in claim 38, wherein said adhesive comprises an epoxy material, and wherein said optically curved element further comprises a protective layer surrounding an edge of said optical layer such that said adhesive is disposed between said optical layer, with said protective layer surrounding said edge thereof, and said supporting surface of said backing plate.

41. The method as recited in claim 38, wherein said minimum thickness x of said adhesive layer is greater than or equal to 20 µm; and said thickness y of said flexible layer is greater than or equal to 5 µm.

42. The method as recited in claim 38, wherein said optical layer comprises a crystal.

43. The method as recited in claim 42, wherein said adhesive layer is an epoxy, and wherein: x is between 0.1 mm and 1 mm and y is between 10 µm and 50 µm.

* * * * *

UNITED STATES PATENT AND TRADEMARK OFFICE
CERTIFICATE OF CORRECTION

PATENT NO. : 6,829,327 B1
DATED : December 7, 2004
INVENTOR(S) : Chen

It is certified that error appears in the above-identified patent and that said Letters Patent is hereby corrected as shown below:

<u>Title page</u>,
Item [57], ABSTRACT,
Line 16, delete "R1" and insert -- R, --

Signed and Sealed this

Second Day of August, 2005

JON W. DUDAS
*Director of the United States Patent and Trademark Office*